United States Patent [19]

Rousseau et al.

[11] 4,158,547

[45] Jun. 19, 1979

[54] METHOD OF SEPARATING COMPONENTS IN A BIOLOGICAL FLUID

[75] Inventors: Robert Rousseau, Laguna Niguel; Charles A. Manganaro, Arcadia, both of Calif.

[73] Assignee: DCA-Diagnostic Corporation of America, Arlington, Tex.

[21] Appl. No.: 695,311

[22] Filed: Jun. 11, 1976

[51] Int. Cl.² .................................. G01N 33/16
[52] U.S. Cl. .......................... 23/230.6; 23/230 B; 210/24; 424/1
[58] Field of Search ............... 23/230 B, 230.6, 230.3; 424/1; 210/42, 51, 54, 24

[56] References Cited
U.S. PATENT DOCUMENTS 3,516,794  6/1970  Murty et al. ...................... 23/230 B
3,666,854  5/1972  Eisentraut ................... 23/230 B UX

OTHER PUBLICATIONS

Tabachnick, "Thyroxine-Protein Interactions," Jour. of Bio. Chem., vol. 239, No. 4, Apr. 1964.

*Primary Examiner*—R. E. Serwin
*Attorney, Agent, or Firm*—Richards, Harris & Medlock

[57] ABSTRACT

Insolubilized serum protein adsorbent, for example bovine serum albumin, of small particle size is an excellent adsorbent for adsorbable components in a biological fluid such as serum. Macroaggregated and polymerized albumin are particularly suited as adsorbents for unbound thyroid hormone in serum and can be used in diagnostic kits for determining total $T_4$ and for $T_3$ uptake.

29 Claims, No Drawings

METHOD OF SEPARATING COMPONENTS IN A BIOLOGICAL FLUID

BACKGROUND OF THE INVENTION

The thyroid gland concentrates inorganic iodine in blood plasma with the ultimate formation of two hormones 3,3',5'-triiodothyronine ($T_3$) and 3,5,3',5'-tetraiodothyronine (thyroxine or $T_4$) in an approximate 1:4 ratio. These hormones are transmitted through the circulatory system to cells where they regulate cell metabolism. In the circulatory system the hormones are in equilibrium with certain proteins in blood serum that bind up the hormone. These proteins are in the main globulin and, to a lesser extent prealbumin and albumin. For example, the equilibrium between $T_4$ and thyroid hormone binding globulin (TBG) can be represented by the equation:

$$T_4 + TBG \rightleftharpoons T_4 \cdot TBG$$

A similar equilibrium for $T_3$ also exists. Thus, in the blood at any given moment is a quantity of bound and unbound $T_3$ and $T_4$. The free hormone is thought to be the biologically active form.

In order to evaluate thyroid function, a number of tests have been developed which are designed to detect the unnatural conditions of hyperthyroidism and hypothyroidism. Among these tests are those designed to measure the total amount of the thyroid hormone $T_4$ since normal limits have been established. An unnaturally high level of $T_4$ is regarded as being indicative of hyperthyroidism whereas an unnaturally low amount indicates hypothyroidism.

Tests for total $T_4$ are not completely reliable indicators of thyroid function. On the one hand, an amount of $T_4$ higher than normal may not be clinically significant if the patient tested also has a higher than normal level of binding protein as occurs during pregnancy or when estrogen containing drugs are being used. On the other hand, a level of $T_4$ within normal limits can exist when total binding protein is low because of liver disfunction and then fail to indicate hyperthyroidism.

In view of the shortcomings in tests for total $T_4$, a complementary test that measures the binding capacity of the serum protein has been developed. This test is known as the $T_3$ uptake test and is designed to measure the binding capacity of TBG in serum.

Both total $T_4$ and $T_3$ uptake tests are conveniently run using well known principles of radioassay. In a typical $T_3$ uptake test, a known quantity of $T_3$ that has been radioactively labeled, usually with $I^{125}$ or $I^{131}$, is admixed with a serum sample wherein it competes with naturally occuring thyroid hormone for binding sites. When equilibrium has been established, bound and unbound $T_3$ are separated from the serum by adding an insoluble adsorbent for unbound $T_3$ to the serum followed by separating the serum and adsorbent. Then the radiation emitted by either the serum containing the labeled and unlabeled TBG bound hormone or the adsorbent containing the unbound portion of the $T_3$ is counted. The amount of radiation emitted is readily correlated to the binding capacity of TBG in the serum.

In a typical total $T_4$ test procedure, the bound thyroxine in serum is separated from the binding proteins by denaturing the complex, for example with alcohol which precipitates the binding proteins leaving about 80% of the $T_4$ in solution in the serum. The serum containing thyroxine is mixed with a buffered solution of TBG and a known amount of labeled $T_4$. The serum $T_4$ and labeled $T_4$ compete for the limited amount of TBG. The sample is then contacted with a suitable insoluble adsorbent for non-TBG bound labeled and unlabeled $T_4$. The serum containing TBG bound $T_4$ and adsorbent are separated and the radiation emitted by one or the other is counted. The amount of radiation emitted is a function of the total $T_4$ in the serum sample.

In both the $T_3$ uptake test and test for total $T_4$, the adsorbent plays a vital role as both tests demand efficient separation between hormone that is bound to protein and free hormone if reproducible accuracy is to be achieved. Thus, among the commercially available diagnostic kits, the principal difference lies in the choice of adsorbent. Adsorbents that have been used include ion exchange resins, for example those disclosed in U.S. Pat. No. 3,414,383. As adsorbents, ion exchange resins suffer from the disability that their avidity for thyroid hormone is so high that they begin to strip thyroid hormone from the TBG or other protein. In addition, a long time, i.e., up to one hour, is required to reach equilibrium. Ion exchange resins also lack a clear end point to distinguish when free hormone is removed and when bound hormone is being stripped from the TBG. There is also an effect of serum aging on the performance of resin tests due to the release of organic acids which can compete with thyroid hormones for binding sites on the resin. See Shaw, W. Hubert, I. L., and Spierto, F. W., *Clin. Chem.*, 22, 673 (1976).

Sephadex, a non-ionic resin gel of crosslinked dextran has also been used. See Murphy and Pattee, *J. Clin. Endo.*, 24, 187 (1964). It has a low affinity for unbound thyroid hormone and, like the ionic exchange resins, requires long equilibrium times.

Other suggested adsorbents are the particulate inorganic crystalline materials described in U.S. Pat. No. 3,666,854. The preferred member of this group is the magnesium silicate known as talc. Equilibrium is rapidly reached using this adsorbent but process variables, i.e., technique of mixing and shaking to keep the serum and talc in contact can result in variations. A principal problem is keeping the talc suspended in the serum as it settles out quickly.

Another proposed method is based upon charcoal as an adsorbent. The charcoal is first treated with a large molecule such as hemoglobin, dextran or the like to fill in the large pores that would adsorb TBG bound hormone as well as the unbound. Charcoal suffers from the disadvantage that equilibrium is never reached and it strips hormone from the binding protein. References to charcoal based techniques are summarized in U.S. Pat. No. 3,721,528. No commercially available test kit presently uses a charcoal adsorbent to measure $T_3$ uptake or total $T_4$ by competitive protein binding.

Another material proposed for use as an adsorbent is microspherical albumin. See Rolleri, et al *J. Nucl. Med.*, 13, 893 (1972). Albumin microspheres are difficult to make, their preparation literally requires the "boiling in oil" of albumin, and are thus economically unattractive. The spheres also have a very low avidity for thyroid hormone requiring a prolonged equilibration time and are difficult to keep in suspension. Thus, for several reasons the microspheres of albumin are not well suited as the adsorbent in a diagnostic test kit.

Many of the adsorbents used in diagnostic kits for evaluating thyroid function are also used in radioassay based on similar techniques where it is necessary to adsorb a component from a body fluid. Thus, the shortcomings they display in that use also occur in other radioassay tests.

From the foregoing it can be seen that the processes known to the prior art for separating adsorbable components from a body fluid are limited in their effectiveness by the shortcomings of the adsorbents previously employed.

OBJECTS OF THE INVENTION

One object of this invention is to provide an improved process for removing adsorbable components from a body fluid and permit measurement of these components.

A more specific object to this invention is to provide an improved process for separating unbound thyroid hormone from hormone bound to a binding protein in serum.

Another object of this invention is to provide an improved radioassay for $T_3$ uptake.

Yet another object of this invention is to provide an improved radioassay for total $T_4$.

Other objects of the invention will become apparent from the following description of the invention.

SUMMARY OF THE INVENTION

The present invention provides a process for removing adsorbable components from a biological fluid. According to the present invention, it has unexpectedly been found that adsorbable components in a biological fluid such as a serum or other body fluid can be conveniently separated from the fluid by contacting the fluid with an insolubilized serum protein adsorbent of near colloidal size capable of forming a finely dispersed suspension. Particularly useful is insolubilized serum albumin such as macroaggregated albumin and finely divided polymeric albumin. Preferably the particles fall within the size range of from 1 to $10\mu$.

The insolubilized serum protein adsorbent is particularly suited as an adsorbent for removing unbound thyroid hormone from a serum. When the serum also contains bound thyroid hormone, equilibrium is rapidly reached and the protein adsorbent does not strip bound thyroid hormone from the binding protein. Because of this, diagnostic radioassays for determining total $T_4$ and for $T_3$ uptake are improved by use of the insolubilized serum protein as the adsorbent.

DETAILED DESCRIPTION OF THE INVENTION

As indicated above, in a broad sense this invention provides a process for separating adsorbable components in a fluid by contacting the fluid with an insolubilized serum protein adsorbent followed by separation of the fluid from the albumin.

The adsorbent suited for use in this invention is particulate protein capable of forming a finely dispersed, precipitable suspension in the fluid containing the adsorbable component. Thus, particles from a near colloidal size up to about $100\mu$ in size are suited. Particles of a size capable of forming a colloidal suspension are not suited as they form a stable suspension from which it is difficult to separate the adsorbent. By contrast, particles larger than about $100\mu$ are difficult to keep in suspension. Preferably, the particles vary from about 1 to $10\mu$ in size as particles of this size easily form finely dispersed suspensions when agitated yet the particles readily settle when the suspension is centrifuged.

The presently preferred forms of serum protein useful in the invention is insolubilized serum albumin such as polymerized albumin and macroaggregated albumin, the latter being particularly preferred. The serum used in the preparation of these forms can be derived from any convenient source. Bovine serum albumin (BSA) is presently preferred because of its ready availability.

Macroaggregated serum albumin is conveniently obtained by the procedure described in Taplin et al, 10 Health Phys. 1219 (1964) and in Taplin et al, J. Nucl. Med. 5, 259 (1964).

Preparation of Macroaggregated Albumin

Serum albumin is diluted with physiological saline solution to a concentration of 1% by volume. The pH is adjusted to $10\pm0.5$ by the addition of 0.2 N NaOH. The solution is heated at 79° C. for 20 minutes with continuous agitation and then cooled to below room temperature by immersion of the vessel in cold water or by other suitable means. The pH is then reduced to 6.0 by adding 0.2 N HCl and then reduced to $5.0\pm0.3$ by the slow addition of 0.2 N HCl with constant agitation. As the pH approaches the isoelectric point, the solution becomes milky and micron sized particles $(1-5\mu)$ form. Centrifuging at about 1500 rpm separates the particles from the fluid. The supernatent containing any colloidal particles is withdrawn and discarded. To obtain particles on the order of $10\mu$, the suspension can be reheated to 79° C. prior to centrifuging.

Procedures for polymerizing albumin are well known. A presently preferred process employs a water soluble carbodimide as a coreactant. A preferred carbodiimide is 1-cyclohexyl-3-(2-morpholinoethyl)-carbodiimide metho-p-toluenesulfonate.

Process For Polymerizing Serum Albumin

BSA (2 grams) and 1-cyclohexyl-3-(2-morpholinoethyl)-carbodiimide metho-p-toluene sulfonate (2 grams) are mixed in deionized water (20 milliliters) and stirred continuously. The pH is adjusted to 5.5 using 0.5 N HCl. After 30 minutes, an additional 1 gram quantity of carbodiimide and 10 ml. of water are added. The pH is maintained at 5.5. After 3 hours, the fibrous material produced was collected by filtration ans washed twice with phosphate buffered saline (pH 7.2). The material was then ground in a teflon tissue grinder and collected by centrifugation and washed twice more with phosphate buffered saline (pH 7.2).

Other suitable methods for polymerizing serum albumin include coreacting it with ethyl chloroformate and difunctional agents such as glutaraldehyde and by diazo coupling.

An application of the process of this invention in a $T_3$ uptake test will now be described. However, it will be appreciated that other uses of this process are within the scope of this invention.

The reagent used in this test is a buffer solution preferably of diethyl barbituric acid (pH 7.4, 0.032 M) in deionized water containing a radioactively labeled $T_3$ as a tracer and a quantity of macroaggregated albumin as the separating agent. The radioactive $T_3$ would preferably be labeled with $I^{125}$ and have a final concentration of 0.02 to 0.20 microcuries per milliliter and 0.1 to 10.0 nanograms per milliliter with a final concentration of 0.5 to 1.0 nanograms per milliliter being particularly preferred. The macroaggregated albumin would be added to a final concentration of 2.5 milligrams per milliliter.

To provide a reference to standardize the assay, a reagent of known value should be included with the test. The reagent preferably would be a standard serum sample of known value and may be supplied in lyophilized form.

A 1.0 ml. aliquot of the combined macroaggregated albumin, barbital buffer and labeled $T_3$ is added to a test tube to which a test sample is to be added. At least one test tube is provided for the standard $T_3$ sample. Preferably, additional test tubes provided for quality control testing of control sera having $T_3$ uptake values in the normal range (25–36%), elevated range (36–40%), and depressed range (22–25%). Such sera are available from commercial sources such as Hyland Laboratories of Costa Mesa, Ca.

Care should be taken to keep the macroaggregated albumin uniformly suspended while withdrawing the 1.0 ml. aliquot of the combined reagent. Stirring, as by use of a magnetic bar, shaking or any other suitable means can be employed.

A 1.0 ml. aliquot of the reagent is added to a test tube containing 0.1 ml. of either patient serum, standard $T_3$ serum or control sera. The test tubes are then agitated as by shaking and/or vortexing to insure uniform mixing. The sample is allowed to stand at room temperature for 5 minutes. Equilibrium is reached during this time but further standing does not affect the result.

After standing, the tube is centrifuged to firmly pack the macroaggregated albumin in the bottom of the tube. Centrifugation at 3000 rpm (1300–1500 g's) is recommended. The test tubes are then decanted to remove the liquid and the radiation emitted by the precipitate is counted. It will be appreciated that other means of separation may be employed. For example, filtration may be used. Also, rather than counting the radiation emitted by the precipitate, the supernatant may be counted.

The radiation emitted by each sample is counted using conventional equipment and background radiation may be subtracted. The emitted radiation of samples of patient sera is converted to percent $T_3$ uptake using the equation:

$$\% \text{ uptake (unknown)} = \text{Counts (unknown)} \times \frac{\% \text{ uptake (standard)}}{\text{Counts (standard)}}$$

The % uptake of the standard is a known value that varies with the particular standard used. This value can be checked by comparison with values obtained for control sera. The testing of control sera also provides an internal check upon the precision of the test as it is conducted in the field.

The $T_3$ uptake test described above has several advantages over other such tests because equilibrium is rapidly reached and because the insolubilized albumin does not strip hormone from TBG. One advantage is that the reagents can be mixed in any order without affecting the result. Because the mixing order is unimportant, labeled $T_3$ and adsorbent can be mixed with the barbital buffer prior to addition to the test tubes. This reduces the number of pipetting steps in an actual assay thereby reducing the chance for error. Because equilibrium is reached during the mixing operation rapid testing is possible. Nevertheless, because the test is unaffected by standing beyond five minutes, a single operator can perform a large number of tests at once.

Those skilled in the art will appreciate that the process of this invention can be used in a test for total $T_4$ by suitable modification using principles well known to the art. The process of this invention is particularly suited for the adsorption from biological fluids of relatively small molecules, i.e., those having a molecular weight on the order of about 20,000 or smaller and particularly is suited for adsorption of molecules having a molecular weight up to about 2,000.

Examples of other assays in which the process of this invention can be employed are assays for digoxin, digitoxin, angiotensin, Vitamin $B_{12}$, folic acid and the like. The determination of the amount of adsorbent and other reagents required in these tests is well within the skill of those in the art. Accordingly, this invention is to be limited only by the scope of the appended claims.

We claim:

1. A process for removing an adsorbable component from a biological fluid comprising contacting the fluid with a portion of insolubilized serum protein adsorbent capable of forming a finely dispersed, precipitable suspension for a time sufficient to adsorb the component.

2. A process according to claim 1 wherein the adsorbent is insolubilized serum albumin.

3. A process according to claim 2 wherein the insolubilized serum albumin is selected from the group consisting of macroaggregated serum albumin and polymerized serum albumin.

4. A process according to claim 1 wherein the particles sizes vary from near colloidal size up to about $100\mu$.

5. A process according to claim 4 wherein the particle sizes vary from about 1 to about $10\mu$.

6. A process according to claim 1 wherein the adsorbent is separated from the fluid after adsorption of the component.

7. A process according to claim 6 wherein separation from the fluid is by centrifuging to precipitate the adsorbent followed by decantation of the liquid.

8. A process according to claim 1 wherein the biological fluid is selected from human and non-human blood serum.

9. A process according to claim 3 wherein the polymerized albumin is a copolymer of serum albumin and a carbodiimide.

10. A process according to claim 9 wherein the carbodiimide is 1-cyclohexyl-3-(2-morpholinoethyl)-carbodiimide metho-p-toluene sulfonate.

11. A process according to claim 1 wherein the adsorbable component has a molecular weight up to about 20,000.

12. A process according to claim 1 wherein the adsorbable component has a molecular weight up to about 2,000.

13. A process according to claim 12 wherein the fluid is blood serum and the adsorbable component is thyroid hormone unbound to serum proteins.

14. A process according to claim 13 wherein the hormone is $T_3$.

15. A process according to claim 13 wherein the hormone is $T_4$.

16. In a radioassay process for determining the binding capacity of serum proteins for thyroid hormone wherein a known quantity of thyroid hormone labeled with a radioactive isotope is added to a serum sample to compete for binding sites on said serum proteins with the thyroid hormone in said sample, the improvement comprising admixing insolubilized serum albumin capable of forming a finely dispersed, precipitable suspension in said serum to adsorb unbound labeled and unlabeled thyroid hormone and separating said insolubilized albumin from said serum containing bound labeled and unlabeled thyroid hormone.

17. A process according to claim 16 wherein the labeled thyroid hormone is $T_3$.

18. A process according to claim 17 wherein the insolubilized serum protein is selected from the group consisting of macroaggregated serum albumin and polymerized serum albumin.

19. A process according to claim 18 wherein the particle size of the insolubilized serum albumin varies from near colloidal size up to about $100\mu$.

20. A process according to claim 19 wherein the particle sizes vary from about 1 to about $10\mu$.

21. A process according to claim 18 wherein the insolubilized albumin is separated from the serum by centrifuging to precipitate the albumin followed by decantation of the liquid.

22. A process according to claim 18 wherein the insolubilized serum albumin and labeled hormone are admixed before mixing with said serum sample.

23. A process according to claim 20 wherein the insolubilized albumin and labeled hormone are admixed in a barbital buffer.

24. A process for measuring $T_4$ in a serum sample comprising:
    (a) treating the sample to denature thyroid binding proteins leaving the $T_4$ in solution in said sample;
    (b) admixing the denatured serum with a known quantity of thyroid binding globulin (TBG) and a known quantity of $T_4$ labeled with a radioactive isotope.
    (c) contacting the admixture of denatured serum, TBG and labeled $T_4$ with a quantity of insolubilized serum albumin capable of forming a finely dispersed, precipitable suspension in said denature serum to adsorb labeled and unlabeled $T_4$ unbound to said TBG;
    (d) separating said insolubilized albumin from said serum; and
    (e) counting the radiation emitted by one of said serum or said insolubilized albumin.

25. A process according to claim 24 wherein the insolubilized serum albumin is selected from the group consisting of macroaggregated albumin and polymerized serum albumin.

26. A process according to claim 25 wherein the particle size of the insolubilized serum albumin varies from near colloidal size to about $100\mu$.

27. A process according to claim 26 wherein the particle sizes vary from about 1 to about $10\mu$.

28. A process according to claim 24 wherein the insolubilized serum albumin, labeled hormone and TBG are admixed prior to mixing with the denatured serum.

29. A process according to claim 28 wherein the insolubilized albumin, labeled hormone and TBG are admixed in a barbital buffer.

* * * * *